United States Patent
Kauppinen et al.

(10) Patent No.: US 9,155,907 B2
(45) Date of Patent: Oct. 13, 2015

(54) APPARATUS AND METHOD FOR COMBINING MACHINE LIMITATIONS INFORMATION WITH TARGET MOTION BOUNDARY INFORMATION

(71) Applicant: Varian Medical Systems International AG, Cham (CH)

(72) Inventors: Juha Kauppinen, Espoo (FI); Johannes Arminen, Helsinki (FI)

(73) Assignee: Varian Medical Systems International AG, Cham (CH)

( * ) Notice: Subject to any disclaimer, the term of this patent is extended or adjusted under 35 U.S.C. 154(b) by 63 days.

(21) Appl. No.: 14/039,721

(22) Filed: Sep. 27, 2013

(65) Prior Publication Data

US 2015/0094513 A1    Apr. 2, 2015

(51) Int. Cl.
*A61N 5/10*    (2006.01)
*A61B 5/00*    (2006.01)
*A61B 6/00*    (2006.01)

(52) U.S. Cl.
CPC .............. *A61N 5/103* (2013.01); *A61N 5/1037* (2013.01); *A61N 2005/1074* (2013.01)

(58) Field of Classification Search
CPC ... A61N 5/1037; A61N 5/1036; A61N 4/106; A61N 5/1045; A61N 5/103
USPC .......... 250/505.1, 492.1, 491.1; 378/65, 147, 378/145
See application file for complete search history.

(56) References Cited

U.S. PATENT DOCUMENTS

| | | |
|---|---|---|
| 2006/0241443 A1* | 10/2006 | Whitmore et al. ............. 600/439 |
| 2009/0041188 A1* | 2/2009 | Keall et al. ....................... 378/65 |
| 2014/0070115 A1* | 3/2014 | Oster et al. ................. 250/492.1 |
| 2014/0275704 A1* | 9/2014 | Zhang et al. ...................... 600/1 |

* cited by examiner

*Primary Examiner* — Nikita Wells
(74) *Attorney, Agent, or Firm* — Fitch, Even, Tabin & Flannery LLP

(57) ABSTRACT

A control circuit accesses machine limitations information and target motion boundary information. The control circuit then combines the machine limitations information with the target motion boundary information when acting with respect to a radiation treatment plan. By one approach the control circuit acts with respect to a radiation treatment plan by presenting machine limitation information in combination with target motion boundary information. As another approach, the control circuit acts by combining the foregoing information while developing the radiation treatment plan to use that information to make automatic adjustments to the radiation treatment plan to correct instances where a planned configuration reveals a conflict between the physical limitations of the treatment platform and the target motion boundary.

21 Claims, 3 Drawing Sheets

APPARATUS AND METHOD FOR COMBINING MACHINE LIMITATIONS INFORMATION WITH TARGET MOTION BOUNDARY INFORMATION

TECHNICAL FIELD

This invention relates generally to the therapeutic irradiation of a patient's target volume.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted areas and adjacent healthy tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient. Such treatment plans are often optimized prior to use. (As used herein, "optimization" will be understood to refer to improving upon a candidate treatment plan without necessarily ensuring that the optimized result is, in fact, the singular best solution.) Many optimization approaches use an automated incremental methodology where various optimization results are calculated and tested in turn using a variety of automatically-modified (i.e., "incremented") treatment plan optimization parameters.

Such radiation-treatment plans typically presume any number of metrics regarding the target volume and/or other organs and tissues in the vicinity of the target volume. Examples of such metrics include, but are not limited to, such things as the size, shape, and orientation of external and/or internal portions of a given organ. These metrics are sometimes developed for a particular patient by referring to previously-obtained x-rays, computed tomography data, and so forth and other times by referring to historical data for other patients or as gleaned from atlases of such content.

Many treatment plans provide for exposing the target volume to radiation from a number of different directions. Arc therapy, for example, comprises one such approach. In such a case it often becomes useful or necessary to also adjust various mechanical components (such as, for example, multi-leaf collimators) of the treatment system when moving the radiation source with respect to the target volume. A radiation-treatment plan therefore often provides information regarding useful or necessary adjustments to various mechanical components of the treatment system during such a treatment.

A radiation-therapy treatment plan for a moving target is typically planned with respect to a static reference geometry where the target volume is presume to be static or where the target volume is integrated over phases of motion (sometimes referred to as Integrated Target Volume (ITV)). The resultant treatment plan geometry is then evaluated using multi-leaf collimator and/or collimator jaws that are set according to a specified static target volume with the assumption that those positions are valid as such. In fact, however, it can be cumbersome or even impossible to ensure that the dosimetrically acceptable target motion boundary associated with such approaches is reachable in all fields and for all treatment directions. In particular, neither the planning apparatus nor the user are necessarily able to glean such information when using prior art approaches in these regards.

BRIEF DESCRIPTION OF THE DRAWINGS

The above needs are at least partially met through provision of the apparatus and method for combining machine limitations information with target motion boundary information described in the following detailed description, particularly when studied in conjunction with the drawings, wherein.

Figure 1:
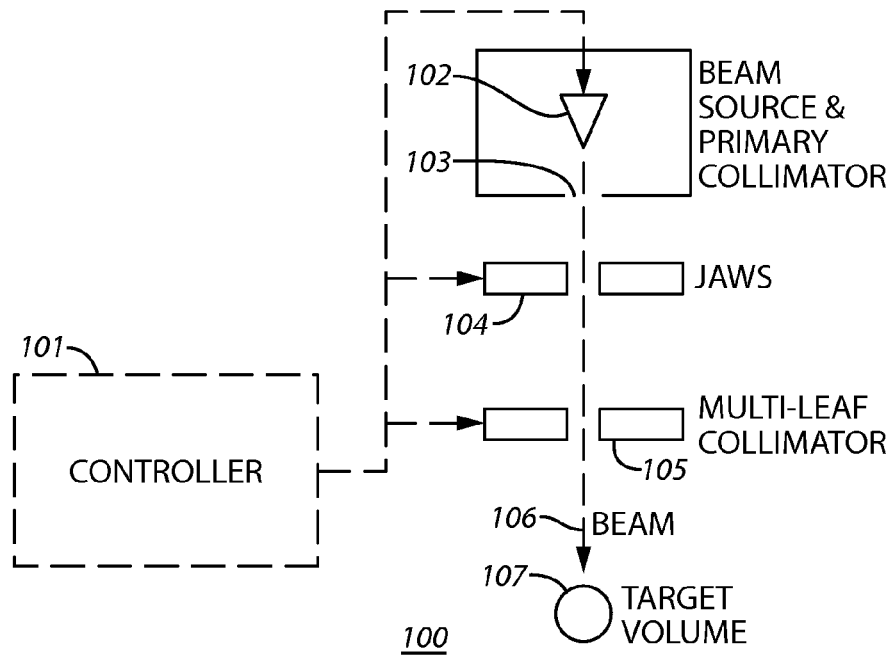
FIG. 1 comprises a block diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a control circuit accesses machine limitations information and target motion boundary information. The machine imitations information pertains to a given radiation-treatment delivery apparatus while the target motion boundary information pertains to a volume within which a radiation target for a given patient may possibly move (for example, as a result of the patient's breathing) during a radiation treatment session via the aforementioned radiation-treatment delivery apparatus. The control circuit then combines the machine limitations information with the target motion boundary information when acting with respect to a radiation treatment plan.

By one approach the control circuit acts with respect to a radiation treatment plan by presenting machine limitation information in combination with target motion boundary information (via, for example, a beam's-eye view display). So configured, an observer can view that presentation and assess whether the planned positions are in fact doable for all fields. As another approach, in lieu of the foregoing or in combination therewith, the control circuit acts with respect to a radiation treatment plan in these regards by combining the foregoing information while developing the radiation treatment plan in order to use that information to make automatic adjustments to the radiation treatment plan to correct instances where a planned configuration reveals a conflict between the physical limitations of the treatment platform and the target motion boundary.

So configured, potential physical conflicts that can otherwise arise due to the physical limitations of the treatment platform in view of possible movement of the target during a treatment session can be largely or even wholly avoided. These teachings are highly flexible in practice and will accommodate a wide variety of variations and modifications. For example, these teachings can be applied in a more static treatment environment if desired. As another example these teachings can be employed to take into account a wide variety of dynamic physical properties of a given treatment platform including, for example, isocenter positioning, collimator angles, field angles, and so forth. As another example, the aforementioned target motion boundary information can comprise information specific to the particular patient (and may have been gleaned, for example, via pre-treatment monitoring) and/or can represent predicted movements based upon studies of other patients or the like.

These and other benefits may become clearer upon making a thorough review and study of the following detailed description. Referring now to the drawings, it may be helpful to first briefly describe and characterize a radiation-treatment delivery apparatus 100 that can serve as an illustrative example in these regards. It will be understood, however, that the specifics of this example are intended to serve only in an illustrative capacity and are not intended to serve as an exhaustive, limiting example as regards the scope of these teachings In this illustrative example a controller 101 of choice controls a number of components including a radiation beam source 102 (which, in this example, includes its own primary collimator 103), a pair (or more) of collimating jaws 104, and at least one multi-leaf collimator 105. Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. In many cases these leaves are configured in pairs where each leaf of a given pair move back and forth co-linearly to one another. Such components are well known in the art and serve to appropriately shape a beam 106 of radiation and deliver that beam 106 to a patient's target volume 107.

Also for the sake of an illustrative example this radiation-treatment delivery apparatus 100 may comprise an arc-based platform. Many treatment plans provide for delivering radiation towards a target tissue from a plurality of different angles. Arc therapy comprises one such approach. Generally speaking, such an approach has the benefit of tending to provide a desired radiation dose to the target volume while lessening the overall radiation impact on any particular non-targeted material by spreading the collateral radiation dose over a larger body of non-targeted material.

Figure 2:
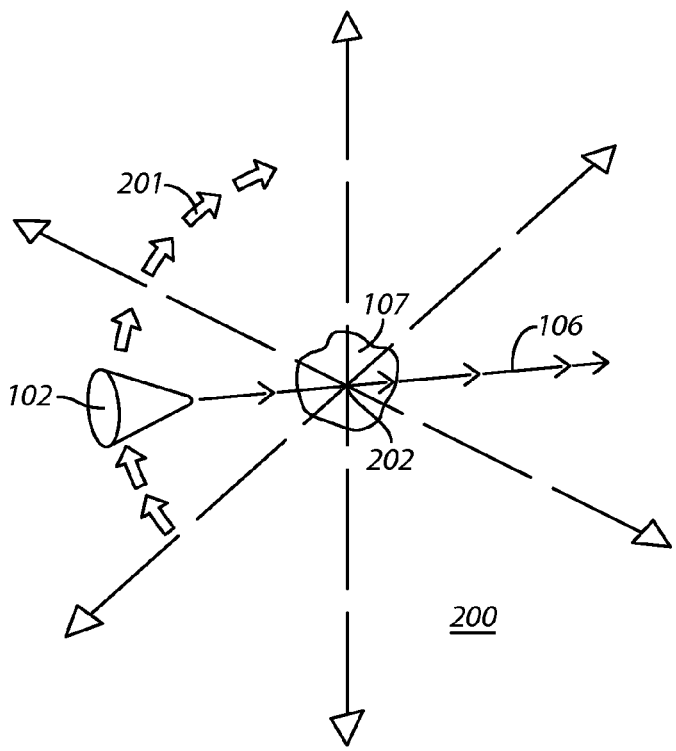
FIG. 2 comprises a perspective schematic as configured in accordance with various embodiments of the invention.

Accordingly, and as generally shown in FIG. 2, during a given treatment session the aforementioned radiation beam source 102 rotates about the target volume 107 by traversing a corresponding arc 201. An X-Y-Z axis 200 helps to illustrate that this rotation occurs about a so-called isocenter 202 of the radiation-treatment delivery apparatus 100. In many cases this isocenter 202 remains stationary with respect to the target volume 107 during a given treatment session but these teachings will also accommodate permitting the isocenter 202 to move with respect to the target volume 107 during a given treatment session as well if desired.

Figure 3:
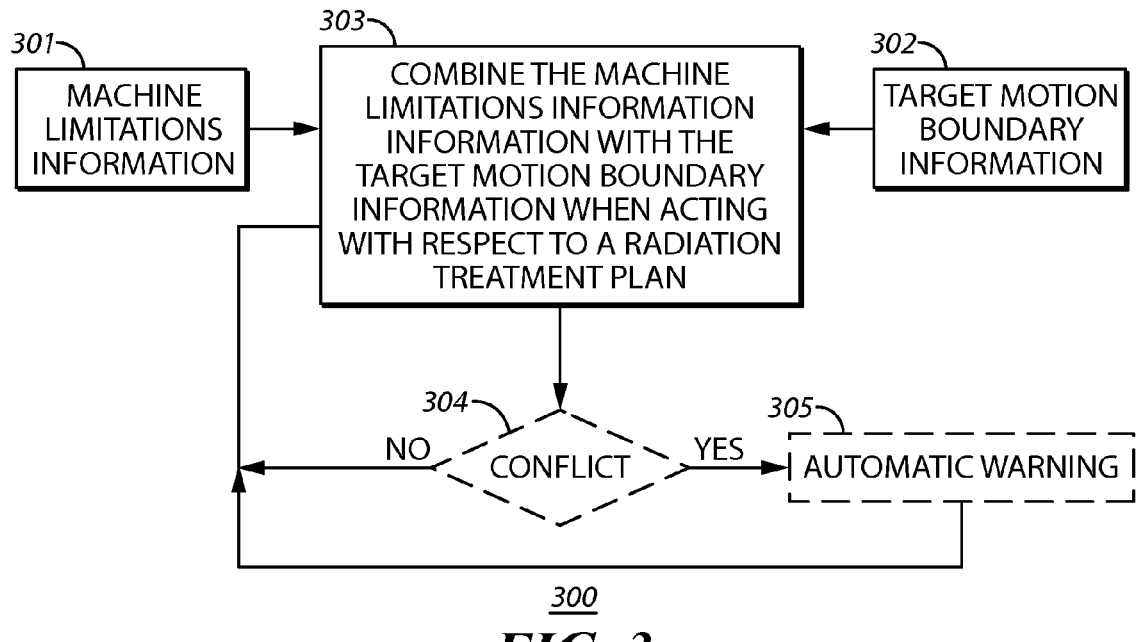
FIG. 3 comprises a flow diagram as configured in accordance with various embodiments of the invention.

FIG. 3 presents a process 300 that can serve with respect to the availability and use of a radiation-treatment delivery apparatus such as (but not limited to) the radiation-treatment delivery apparatus 100 described above. This process 300 provides for the availability of machine limitations information 301 as pertains to the radiation-treatment delivery apparatus 100. The specifics of this information will of course vary from one platform to another and can also vary with the design preferences of the administrator as well.

By one approach, the machine limitations information 301 can include one or both of information regarding the range of motion for the multi-leaf collimator 105 and the range of motion for the pair of collimating jaws 104. Examples in these regards include, but are not limited to, the furthest-most position to which the leaves of the multi-leaf collimator 105 can be withdrawn.

By one approach the machine limitations information can represent such machine limitations at each of the plurality of fields along the radiation-treatment arc 201 described above. It will also be understood that these teachings are similarly applicable for use with static treatment fields as occur when using constant gantry and patient couch angles.

This process 300 also provides for the availability of target motion boundary information 302. This target motion boundary information 302 represents target motion boundaries for the target volume 107, and typically at each of the plurality of fields that characterize a radiation-treatment arc 201. Accordingly, the target motion boundary for a given target volume 107 is typically a volume that is larger than the target volume 107 itself, that fully subsumes the target volume 107, and that represents the furthest extent to which the target volume 107 will (likely or absolutely, as the case may be) move during the course of a radiation-treatment session.

The aforementioned movement can be owing to any of a variety of voluntary and involuntary movements of the patient themselves. It is also possible for such movement to be owing, in whole or in part, to relative movement of the couch upon which the patient rests during the session. Accordingly, in many cases the target motion boundary information 302 is specific to a particular patient for whom the radiation treatment plan is being developed.

In many cases the radiation-treatment delivery apparatus 100 has the ability to track such movement. For example, the apparatus 100 can have sensors that are configured to track radio-frequency transducers that are implanted within the particular patient (for example, by being implanted in, or near, the target volume 107). The Calypso® system as offered by Varian is one example in these regards. In such a case, the aforementioned target motion boundary information can be developed, at least in part, by tracking such transducers (prior to the treatment session itself and/or on-the-fly during the course of the treatment session).

This process 300 then provides for a control circuit of choice to combine the foregoing machine limitations information with the target motion boundary information when acting with respect to a radiation treatment plan. Generally speaking, this combining of information can serve to identify, globally and/or on a field-by-field basis, treatment scenarios where the target volume 107 has the noted potential to move to a location that places at least part of the target volume 107 outside the footprint of the beam 106. Note that this analysis does not necessarily rely upon a conclusion that the target volume 107 will for a certainty be at least partially unexposed to the beam 106. Instead, this process 300 can act when only the possibility of such an event exists.

The specific nature of the foregoing combination and resultant action can vary as desired with respect to the application setting and the preferences of the planning and/or treatment administrator. By one approach, and referring momentarily to FIG. 4, this activity can comprise, at least in part, simultaneously presenting the machine limitations information in combination with the target motion boundary information in a corresponding visual depiction 400. In this particular illustrative example the visual depiction 400 comprises a beam's-eye view display. It will be appreciated, however, that these teachings will accommodate other approaches in these regards as well as desired. For example, the visual depiction 400 can instead comprise an orthogonal two-dimensional or three-dimensional view, an arc plane view, and so forth. Also in the present illustrative example it is presumed that the process 300 provides such a visual depiction 400 at each of a plurality of fields along a radiation-treatment arc 201 as described above.

In particular, each such visual depiction 400 can present a depiction of the target volume 107 and its spatial relationship to the aforementioned isocenter 202. A delineated area 401 represents the target motion boundary information 302 (keeping in mind that the illustrated representation is a two-dimensional view that presents this delineated area 401 as a two-dimensional area). By one approach this view can include three-dimensional information as well using any of a variety of three-dimensional display techniques as are known in the art. The shape of the delineated area 401 can of course be irregular and nonsymmetrical as the target motion boundary information 302 can vary considerably in these regards for a given patient.

Figure 4:
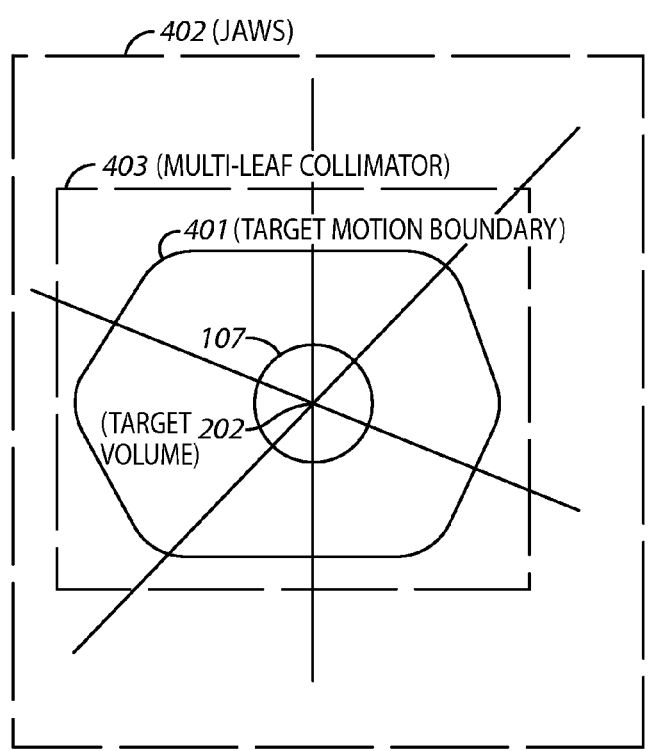
FIG. 4 comprises a schematic screenshot as configured in accordance with various embodiments of the invention.

The visual depiction 400 of FIG. 4 presents the machine limitations information 301 as a first aperture 402 that represents the aforementioned collimator jaws 104 and a second aperture 403 that represents the aforementioned multi-leaf collimator 105. So configured, the user can readily determine by visual examination whether the latter apertures 402 and 403 will accommodate the target motion boundaries 401 and hence whether the radiation-treatment delivery apparatus 100 is physically capable (at least at this particular field) of accommodating whatever movement of the target may occur during actual administration of the plan. Upon determining that such is not the case for one or more fields, the user can take an appropriate action to modify the treatment plan (either in a direct way, such as by specifying a particular parameter setting(s) or in an indirect way, such as by prompting the planning process to continue iterating in search of a more optimum solution).

By another approach, and referring again to FIG. 3, the aforementioned activity can comprise, at least in part, automatically detecting at 304 when a conflict exists in the foregoing regards (i.e., when it is possible for the target volume 107 to move beyond the available aperture settings for either the collimator jaws 104 or the multi-leaf collimator 105). In such a case, at 304 the process 300 can automatically provide a warning when the machine limitations information 301 conflicts with the target motion boundary information 302 (either globally and/or on a field-by-field basis as desired). The nature of this warning can vary as desired with examples including but not limited to audible alerts, visual alerts, haptic alerts, automated text/email messages, and so forth and can be provided at times deemed appropriate by the developer or user (such as during planning, post-planning but pre-treatment, during treatment, and so forth).

By another approach, the process 300 can respond to such a conflict when developing the radiation treatment plan by using that information to make automated adjustments to the radiation treatment plan (for example, as part of an optimization process). The present teachings will accommodate a wide variety of automated adjustments in these regards. Examples include but are not limited to adjusting one or more of:

a radiation treatment machine isocenter position (for example, by translating, rotating, raising, or lowering the patient support couch);

a collimator angle;

a field angle (for example, by adjusting the gantry and/or patient support couch);

a collimator jaw position (for example, by increasing or reducing the distance of the collimator jaw with respect to the radiation source); and one or more multi-leaf collimator leaf positions (for example, on a leaf-pair basis including but not limited to leaf positions when pairs of leaves meet one another).

So configured, machine limitations is used in combination with target motion boundary information to access and determine when and if conflicts can potentially arise with respect to the potential position of a target volume with respect to the physical ability of the radiation-treatment delivery apparatus to fully dose the target volume (including at each of a plurality of sequential fields as comprise, for example, a treatment arc). The resultant information in these regards can be simply provided to a human observer if desired and/or can be automatically acted upon in any of a variety of ways (including as part of the planning process when optimizing machine settings to facilitate delivering the desired dose to the target volume while simultaneously minimizing collaterally dosing to non-targeted patient areas.

Figure 5:
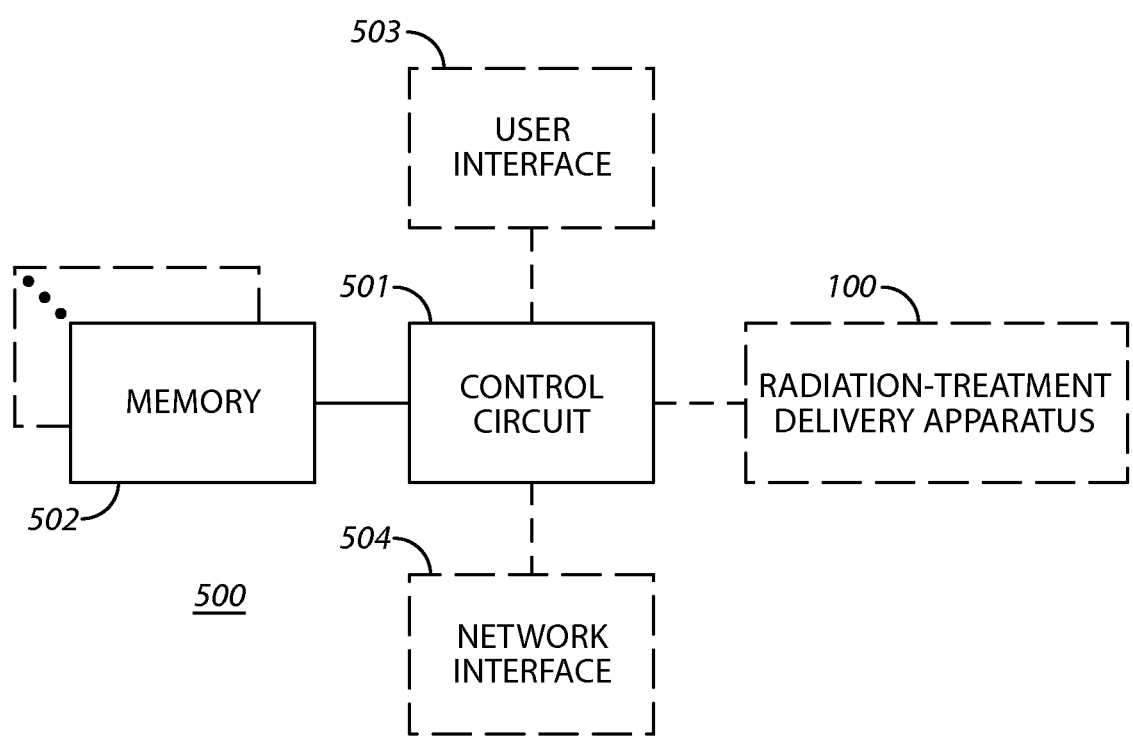
FIG. 5 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 5, an illustrative approach to such a platform 500 will now be provided.

Such a platform 500 may be comprised of a plurality of physically distinct elements as is suggested by the illustration shown in FIG. 5. It is also possible, however, to view this illustration as comprising a logical view, in which case one or more of these elements can be enabled and realized via a shared platform. It will also be understood that such a shared platform may comprise a wholly or at least partially programmable platform as are known in the art.

In this example the platform 500 includes a control circuit 501 that operably couples to one or more memories 502. Such a control circuit 501 can comprise a fixed-purpose hard-wired platform or can comprise a partially or wholly programmable platform. These architectural options are well known and understood in the art and require no further description here. This control circuit 501 is configured (for example, by using corresponding programming as will be well understood by those skilled in the art) to carry out one or more of the steps, actions, and/or functions described herein.

The memory 502 may be integral to the control circuit 501 or can be physically discrete (in whole or in part) from the control circuit 501 as desired. This memory 502 can also be local with respect to the control circuit 501 (where, for example, both share a common circuit board, chassis, power supply, and/or housing) or can be partially or wholly remote with respect to the control circuit 501 (where, for example, the memory 502 is physically located in another facility, metropolitan area, or even country as compared to the control circuit 501).

This memory 502 can serve, for example, to non-transitorily store the aforementioned machine limitations information 301 and/or the target motion boundary information 302 as well as computer instructions that, when executed by the control circuit 501, cause the control circuit 501 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

By one optional approach the control circuit 501 operably couples to a user interface 503. This user interface 503 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

Also, and as another optional approach, the control circuit 501 can operably couple to a network interface 504. This network interface 504 can comprise a wireless and/or a non-wireless interface as desired. So configured, for example, the control circuit 501 can communicate via a local network and/or an external network (such as the Internet). Such a network interface 504 can facilitate, for example, receiving some or all of the machine limitations information 301 and the target motion boundary information 302 and/or transmitting information regarding the aforementioned conflicts and corresponding action as desired.

And as yet another optional approach, the control circuit 501 can operably couple to the aforementioned radiation-treatment delivery apparatus 100. So configured, the control circuit 501 can, for example, directly control the operation of the radiation-treatment delivery apparatus 100 in accordance with a developed radiation-treatment plan.

So configured, these teachings permit, for example, a computer to serve when using geometrical treatment planning and where target structures are tracked during treatment delivery that relies upon the dynamic movement of multi-leaf collimator leaves and/or collimator jaws. In particular, these teachings facilitate identifying instances when conflicts between what the radiation-treatment delivery apparatus is physically capable of accomplish and where the target volume may potentially move.

Those skilled in the art will appreciate the practical flexibility of these teachings. For example, by one approach, the machine limits could serve to shape the relevant target motion boundary. In such a case, instead of making adjustments in the machine/treatment geometry the tracking limits could be adjusted according to the machine limits. In such a case and by one approach the tracking limits could be primarily (or at least initially) based on dose evaluation but could also be further limited by machine limits. For example, upon establishing the total target motion boundary the process could then determine a dosimetrically acceptable target motion boundary. This could then lead to determining a dosimetrically acceptable and treatable target motion boundary and corresponding tracking limits that will be effective during treatment delivery (where "treatable" refers to whether the machine can track the target within the boundary using the same considerations presented above per the present teachings). Using this approach, for example, whenever the target travels outside the tracking limits the radiation beam can be turned off.

Those skilled in the art will recognize that a wide variety of other modifications, alterations, and combinations can be made with respect to the above described embodiments without departing from the scope of the invention, and that such modifications, alterations, and combinations are to be viewed as being within the ambit of the inventive concept.

What is claimed is:

1. An apparatus comprising:
a memory having stored therein machine limitations information as regards a radiation-treatment delivery apparatus and target motion boundary information as regards a volume within which a radiation target may possibly move during a radiation treatment session via the radiation-treatment delivery apparatus;
a control circuit operably coupled to the memory and configured to act with respect to a radiation treatment plan based on a combination of the machine limitations information and the target motion boundary information.

2. The apparatus of claim 1 wherein the machine limitations information comprises information regarding at least one of:
range of motion for a multi-leaf collimator; and
range of motion for a pair of collimating jaws.

3. The apparatus of claim 2 wherein the machine limitations information comprises information regarding both of:
range of motion for a multi-leaf collimator; and
range of motion for a pair of collimating jaws.

4. The apparatus of claim 1 wherein the machine limitations information represents machine limitations at each of a plurality of fields along a radiation-treatment arc.

5. The apparatus of claim 1 wherein the target motion boundary information represents target motion boundaries for the volume at each of a plurality of fields along a radiation-treatment arc.

6. The apparatus of claim 1 wherein the target motion boundary information comprises information specific to a particular patient for whom the radiation treatment plan is being developed.

7. The apparatus of claim 6 wherein the target motion boundary information comprises information developed, at least in part, by tracking radio-frequency transducers implanted within the particular patient.

8. The apparatus of claim 1 wherein the control circuit is configured to combine the machine limitations information with the target motion boundary information by, at least in part, simultaneously presenting the machine limitations information in combination with the target motion boundary information in a beam's-eye view display.

9. The apparatus of claim 8 wherein the control circuit is further configured to simultaneously present the machine limitations information in combination with the target motion boundary information in a beam's-eye view display by, at least in part, simultaneously presenting the machine limitations information in combination with the target motion boundary information in a beam's-eye view display at each of a plurality of fields along a radiation-treatment arc.

10. The apparatus of claim 1 wherein the control circuit is further configured to:
provide an automatic warning when the machine limitations information conflicts with the target motion boundary information.

11. The apparatus of claim 10 wherein the control circuit is further configured to provide an automatic warning when the machine limitations information conflicts with the target motion boundary information at any of a plurality of fields along a radiation-treatment arc.

12. The apparatus of claim 1 wherein the control circuit is configured to combine the machine limitations information with the target motion boundary information when developing a radiation treatment plan in order to use that information to make adjustments to the radiation treatment plan.

13. The apparatus of claim 12 wherein the control circuit is configured to make the adjustments to the radiation treatment plan by adjusting at least one of:
- a radiation treatment machine isocenter position;
- a collimator angle;
- a field angle;
- a collimator jaw position; and
- at least one multi-leaf collimator leaf position.

14. A method comprising:
by a control circuit:
- accessing a memory having stored therein machine limitations information as regards a radiation-treatment delivery apparatus and target motion boundary information as regards a volume within which a radiation target may possibly move during a radiation treatment session via the radiation-treatment delivery apparatus;
- combining the machine limitations information with the target motion boundary information when acting with respect to a radiation treatment plan.

15. The method of claim 14 wherein the machine limitations information comprises information regarding at least one of:
- range of motion for a multi-leaf collimator; and
- range of motion for a pair of collimating jaws.

16. The method of claim 14 wherein the machine limitations information represents machine limitations at each of a plurality of fields along a radiation-treatment arc.

17. The method of claim 14 wherein the target motion boundary information represents target motion boundaries for the volume at each of a plurality of fields along a radiation-treatment arc.

18. The method of claim 14 wherein combining the machine limitations information with the target motion boundary information comprises, at least in part, simultaneously presenting the machine limitations information in combination with the target motion boundary information in a beam's-eye view display.

19. The method of claim 18 wherein simultaneously presenting the machine limitations information in combination with the target motion boundary information in a beam's-eye view display comprises, at least in part, simultaneously presenting the machine limitations information in combination with the target motion boundary information in a beam's-eye view display at each of a plurality of fields along a radiation-treatment arc.

20. The method of claim 14 further comprising:
providing an automatic warning when the machine limitations information conflicts with the target motion boundary information.

21. The method of claim 20 wherein providing an automatic warning when the machine limitations information conflicts with the target motion boundary information comprises providing the automatic warning when the machine limitations information conflicts with the target motion boundary information at any of a plurality of fields along a radiation-treatment arc.

\* \* \* \* \*